United States Patent [19]

Lidgren

[11] Patent Number: 6,075,067
[45] Date of Patent: Jun. 13, 2000

[54] CEMENT FOR MEDICAL USE, METHOD FOR PRODUCING THE CEMENT, AND USE OF THE CEMENT

[75] Inventor: Lars Ake Alvar Lidgren, Lund, Sweden

[73] Assignee: Corpipharm GmbH & Co, Dieburg, Germany

[21] Appl. No.: 08/923,024

[22] Filed: Sep. 3, 1997

Related U.S. Application Data

[63] Continuation-in-part of application No. 08/697,431, Aug. 23, 1996, abandoned, which is a continuation of application No. 08/290,555, Aug. 15, 1994, abandoned.

[51] Int. Cl.$^7$ .............................. A61K 33/08; A61K 9/14
[52] U.S. Cl. ..................... 523/116; 523/113; 523/114; 523/115; 523/117; 524/413; 524/417; 524/431; 524/436; 424/426
[58] Field of Search ....................... 523/113, 114, 523/115, 116, 117; 524/413, 417, 431, 436; 424/426

[56] References Cited

U.S. PATENT DOCUMENTS

| | | | |
|---|---|---|---|
| 4,503,169 | 3/1985 | Randklev | 523/115 |
| 4,588,583 | 5/1986 | Pietsch et al. | |
| 4,668,295 | 5/1987 | Bajpai . | |
| 4,722,948 | 2/1988 | Sanderson . | |
| 4,927,866 | 5/1990 | Purman et al. | |
| 5,114,240 | 5/1992 | Kindt-Larsen et al. | |
| 5,125,971 | 6/1992 | Nonami et al. | 106/35 |
| 5,258,420 | 11/1993 | Posey-Dowty et al. | |
| 5,264,215 | 11/1993 | Nakabayashi et al. | 523/115 |
| 5,370,221 | 12/1994 | Magnusson et al. | |
| 5,374,427 | 12/1994 | Still et al. | |
| 5,398,483 | 3/1995 | Smith et al. | |
| 5,763,092 | 6/1998 | Lee et al. | 428/469 |

FOREIGN PATENT DOCUMENTS

| | | |
|---|---|---|
| 0190504 | 8/1986 | European Pat. Off. . |
| 0242672 | 10/1987 | European Pat. Off. . |
| 0301759 | 2/1989 | European Pat. Off. . |
| 0425200 | 5/1991 | European Pat. Off. . |
| 0511868 | 11/1992 | European Pat. Off. . |
| 2606282 | 5/1988 | France . |
| 3730298 | 5/1988 | Germany . |
| 4016135 | 11/1990 | Germany . |
| 2947875 | 7/1992 | Germany . |
| 2156824 | 10/1985 | United Kingdom . |

*Primary Examiner*—Andrew E. C. Merriam
*Attorney, Agent, or Firm*—Tarolli, Sundheim, Covell, Tummino & Szabo L.L.P.

[57] ABSTRACT

In a method for producing a cement for medical use, a liquid component containing a polymerizable substance is combined with a solid component comprising a plastic substance to provide a setting mass to form the cement. In order to e.g. improve the biological and mechanical properties of the cement and allow it to be mixed by modern mixing procedures, which further improves the cement quality, said plastic substance is mixed with a particulate crystalline ceramic material prior to combining said liquid and solid components. A cement for medical use is also defined as is the use of set cement as an anchorage for the fixation of prostheses or parts of prostheses or bone and as a substitute material for bone.

20 Claims, 1 Drawing Sheet

CEMENT FOR MEDICAL USE, METHOD FOR PRODUCING THE CEMENT, AND USE OF THE CEMENT

This application is a continuation-in-part of application (s) Ser. No. 08/697,431, filed on Aug. 23, 1996, now abandoned, which is a file Wrapper Continuation of U.S. Ser. No. 08/290,555, filed Aug. 15, 1994 (now Abandoned).

BACKGROUND OF THE INVENTION

This invention relates to a method for producing a cement for medical use according to which a liquid component containing a polymerizable substance is combined with a solid component comprising a plastic substance to provide a setting mass to form the cement. The polymerizable substance of the liquid component is generally monomer methacrylate and the plastic substance of the solid component is generally polymer methacrylate. In the present invention, a crystalline ceramic material is mixed with the plastic substance before combining the solid and liquid components.

The invention also relates to a cement for such uses and to the use of set cement as an anchorage for the fixation of prostheses or parts of prostheses or bone and as a substitute material for bone.

The use of anchorage substances in surgical procedures, especially for implants, has led to the development of so-called bone cement. The most common use of bone cement has been to fill the gap between a joint implant and tissue, primarily bone. As the cement sets around an implant immediate fixation will be achieved. When bone cement is used, weight bearing is generally allowed within the first postoperative days. The most important complication hitherto has been infection, joint implants breakage or dislocation. Through strict aseptic and antiseptic measures and methodologic development, the most severe problems today are wear of the polymer component and loosening between the metallic and polymer implants and bone leading to an interface failure with bone resorption and loss of implant anchorage. An improvement of material and technique has been going on since joint implant procedure with the bone cement started in the late 1950's through cooperation between researchers, engineers, manufacturers and surgeons.

The most important development in the area of bone cement has been a change of the additives used in bone cement. Various substances with particles between 20–300 micrometers in size have been used. Particulate additive powder has mainly been used in a spherical form. This may be regarded as the accepted technique today. Both resorbable particulate powder such as tri-calcium phosphate and non resorbable powder such as zirconium oxide have been used. The addition of particulate powder varies between about 5% to about 30% with about 20% to about 25% being the preferred amount. In contrast to the additives which have a secondary role, for example zirconium oxide or barium sulphate which produce a radiopaque bone cement, and tri-calcium phosphate which produces a porous cement, new additives will have to be developed to improve both the biological and mechanical properties of bone cement.

SUMMARY OF THE INVENTION

The aim of this invention has been to develop additives which improve the mechanical properties of bone cement and the tissue interface reaction giving a quicker bone or tissue in-/ongrowth to the implant.

A further aim has been to reduce the radioactivity from zirconium oxide but still allow the bone cement to be mixed by modern mixing procedures, which further improves cement quality and reduces monomer exposure in the operating area.

BRIEF DESCRIPTION OF THE DRAWINGS

Further features of the present invention will become apparent to those skilled in the art to which the present invention relates from reading the following specification with reference to the accompanying drawing, in which.

DETAILED DESCRIPTION OF THE PREFERRED DRAWINGS

Figure 1:
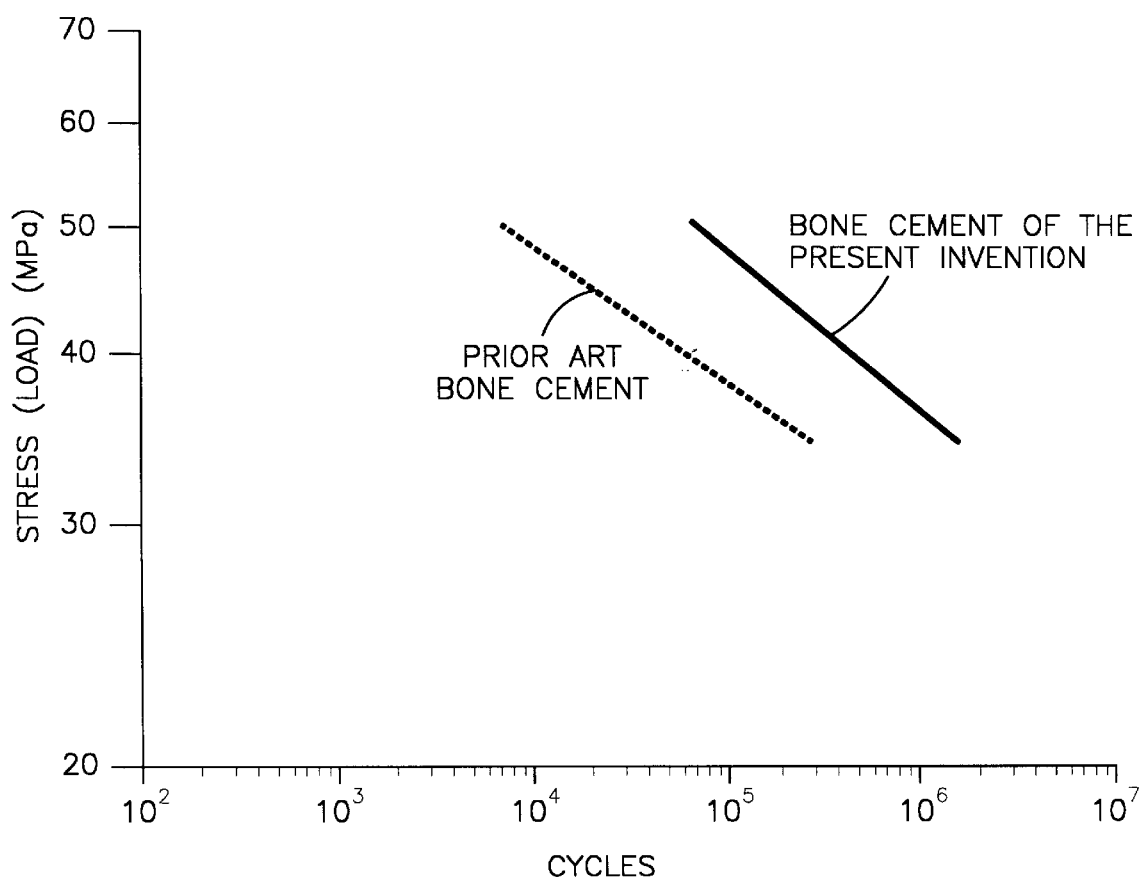
FIG. 1 is a graph comparing fatigue strength of prior art bone cement to bone cement of the present invention.

Adding crystalline ceramic particulate powder to the polymer methacrylate will resolve some of the problems stated above. It is important that the crystalline ceramic material of the present invention comprise about 95% crystalline material and about 5% amorphous material. Conventional crystalline ceramic materials usually comprise about 70% crystalline material and about 30% amorphous material. The amorphous material in the crystalline ceramic material goes into solution in the human body, thereby weakening the ceramic material. Thus, since the bone cement of the present invention is made with a crystalline ceramic material having a greater proportion of crystalline material than the conventional crystalline ceramic materials, the bone cement of the present invention will have greater strength characteristics than conventional bone cement.

The crystalline ceramic materials for use with the present invention, comprising about 95% crystalline material and about 5% amorphous material, include calcium phosphate, zirconium oxide or non-ionic contrast aids, hydroxyl apatite, alumina, metallic ceramics and combinations thereof.

Preferably, the crystalline ceramic additive is produced in the classic way in the temperature curve span where the sintering of particulate powder takes place. It excludes dried powder or powder produced through agglomeration. Ceramic powder for bone cement may be produced in two different ways. The first possibility is to produce a synthetic or biological powder with the requested homogeneity followed by sintering in an oven. The sintered beads will then be ground, a procedure that is technically known. After selection of the distribution and size of beads, the crystalline ceramic powder is added to the bone cement. The second possibility is to use the above described powder together with water or other solutions in order to get a dough with a microporosity through a special working procedure which dough then will be sent for drying. The mixture will be sintered in the classic way. Preferably, in the following description of the invention the first method is used.

To improve the interface and the biological tissue ingrowth, it is according to the invention important that the size of the beads be smaller than those previously used in the art.

At least 50% of the added beads should be less than 50 micrometers with a gaussian curve of distribution and at least 50% of the above additive should be less than 3 micrometers. By using this bead size and distribution, the rheological properties of the invented bone cement will be enhanced and the contact area increased at the cement surface. This allows for a rapid tissue ingrowth. It is possible to add further separate crystalline ceramic additives according to the procedure above.

Antibiotics containing bone cement have been used since the beginning of the 70's. The antibiotic granulate is dissolved from the surface of the one cement. This gives a high antibiotic tissue concentration thereby killing bacteria pre- and postoperatively. The antibiotics may be administered in the bone cement in three different ways. The first way is to add powder to the cement.

The second way is to add antibiotics to the separate crystalline ceramic beads through a pharmaceutical procedure as for instance after soaking in an antibiotic solution. The antibiotics will then be administered into bone cement together with crystalline powder. By this procedure the antibiotics will be at the surface of the additive. This gives the advantage of administering antibiotics with extremely variable acting mechanisms. It is also possible to use a combination of antibiotics both in the bone cement as a powder as well as by integration into the additive ceramic crystalline powder.

The third possibility is to add antibiotics as a solution to the bone cement.

Finally, to avoid absorption of monomer fluid to a considerable extent by the porous particles, the pores can be filled with monomerizable material with a low consistency. After polymerization it might be necessary to grind the material in order to achieve the desired particle size.

The possibility of using cement application in humans today depends on whether or not it could be used in delivery systems, especially in combination with a vacuum. This could be achieved by using an appropriate viscosity (rheological properties) of the bone cement. The bone cement defined above will preferably be used together with a vacuum and injected into humans through a delivery system with a cement viscosity that allows for this procedure.

By using the bone cement according to the invention in a closed system during mixture and delivery, no transfer of the bone cement is necessary. One such suitable system is a so-called Prepack in which the solid and liquid components are contained separated from each other in different individual chambers within one and the same container, wherein the chambers are connected to each other when the components are to be combined.

By adding heat to the bone cement during the mixing procedure the setting time will be reduced; and by chilling the bone cement the setting time will be increased. By using different temperature intervals it will be possible to individualize the setting time of the above described bone cement according to the invention.

The preferred use of the above described bone cement is to be used in anchoring joint implants or bone and as a bone substitute.

EXAMPLE 1

A synthetically produced hydroxyl apatite powder is mixed with a synthetic zirconium oxide in a proportion of 8:2. The powder is heated to 1250° C. with a soft powder shaking procedure. This is followed by a grinding procedure and a classification of the powder. As an example, 5 g of the crystalline ceramic beads thus produced will be added to 35 g of bone cement to achieve polymerization and the monomer will be filed separately.

EXAMPLE 2

As example 1 with the exception that zirconium oxide is replaced with aluminum oxide.

EXAMPLE 3

As in example 1 in which a non-ionic crystalline X-ray contrast aid preferably LOHEXOL, an iohexol commercially produced by Shering, LOHEXOL, which is a radio-opaque substance, is used instead of zirconium oxide.

EXAMPLE 4

As in example 1 in which crystalline ceramic calcium phosphate is used instead of zirconium oxide.

EXAMPLE 5

As in example 1—4 with the exception that a metallic ceramic powder is used.

EXAMPLE 6

As example 1–5 with an antibiotic powder added.

EXAMPLE 7

As example 1–6 where the monomer is mixed with an addition of antibiotics.

EXAMPLE 8

As in example 1–4 with crystalline ceramic powder which is soaked and dried with antibiotics prior to the mixing.

EXAMPLE 9

10 g of crystalline particles are soaked with methyl methacrylate containing a polymerization starting system. After curing for 24 hours, the material is ground, classified and added to the bone cement in order to get 5 g of crystalline ceramic in 45 g of polymer powder.

The fatigue behavior of prior art bone cement and bone cement of the present invention was tested under load controlled conditions. Bar-shaped test specimens (75 mm×10 mm×3 mm) were prepared and stored in a physiological medium (Ringers solution) at temperatures of 37° C. for at least four weeks until equilibrium in water uptake was achieved.

Fatigue behavior was investigated following Wohler's procedure by applying a sinusoidal pulsating loading at a frequency of 5 Hz. At different constant load amplitudes the number of cycles until fracture was recorded.

The results are plotted in FIG. 1. The x-axis shows the number of cycles and the y-axis shows the applied load.

As can be seen in FIG. 1, the bars made of bone cement of the present invention can endure about ten times more cycles before fracturing than the bars made of the prior art bone cement. Thus, the fracture resistance, and thus the long term stability (endurance), of the bone cement of the present invention is greatly improved relative to the prior art bone cement.

From the above description of the invention, those skilled in the art will perceive improvements, changes and modifications. Such improvements, changes and modifications within the skill of the art are intended to be covered by the appended claims.

Having described the invention, the following is claimed:

1. Method for producing a cement for medical use, in which a liquid component comprising a polymerizable substance is combined with a solid component comprising a plastic substance to provide a setting mass which is set to form the cement, wherein said plastic substance is mixed with a particulate crystalline ceramic material prior to combining said liquid and solid components, each particle of said crystalline ceramic material comprising about 95% crystalline material and about 5% amorphous material.

2. Method according to claim 1, wherein said particulate crystalline ceramic material is selected from the group consisting of calcium phosphate, zirconium oxide or non-ionic X-ray contrast aids, hydroxyl apatite, alumina, metallic ceramics and combinations thereof.

3. Method according to claim 2, wherein said particulate crystalline ceramic material is a mixture of calcium phosphate/alumina or calcium phosphate/zirconium oxide.

4. Method according to claim 2, wherein crystalline ceramic calcium phosphate is mixed with a non-ionic X-ray contrast aid.

5. Method according to claim 4, wherein at least about 50% of the particulate material has a particle size of less than about 20 microns.

6. Method according to claim 4, wherein the particle size distribution of said particulate material generally follows a regular distribution.

7. Method according to claim 6, wherein at least about 50% of the regular distributed particles have a particle size of less than about 3 microns.

8. Method according to claim 1, wherein an antibiotic or a mixture of antibiotics is contained in either of said solid or liquid components.

9. Method according to claim 1, wherein said solid and liquid components are contained or packed in different individual chambers of a container.

10. Method according to claim 9, wherein a communication is provided between said individual chambers so as to bring about the mixing of said solid and liquid components within the container.

11. Method according to claim 1, wherein the setting characteristic of the setting mass is adjusted through the supply or withdrawal of heat.

12. A cement for medical use comprising:
    a liquid component which comprises a polymerizable substance; and
    a solid component which comprises a plastic substance and particulate crystalline ceramic material,
    wherein said plastic substance provides a setting mass which is set to form the cement, and wherein each particle of said crystalline ceramic material comprises about 95% crystalline material and about 5% amorphous material.

13. Cement according to claim 12, wherein said crystalline ceramic material is selected from the group consisting of calcium phosphate, zirconium oxide, hydroxyl apatite, alumina, metallic ceramics, non-ionic X-ray contrast aids or combinations thereof.

14. Cement according to claim 12, wherein said ceramic material is an X-ray contrast aid.

15. Cement according to claim 12, wherein said cement also contains an antibiotic or a mixture of antibiotics.

16. Cement according to claim 12, wherein at least about 50% of said ceramic material has a particle size of less than about 20 microns.

17. Cement according to claim 12, wherein the particulate crystalline ceramic material has particle sizes distributed in accordance with a regular distribution.

18. Cement according to claim 17, wherein at least about 50% of said particulate material has a particle size of less than about 3 microns.

19. Method according to claim 1, wherein the particulate crystalline ceramic material is mixed with acrylate and the setting mass is ground to a particle size wherein at least about 50% of the particulate material has a particle size of less than about 20 microns.

20. Method according to claim 12, further comprising the step of applying the setting mass to a bone or prostheses; and wherein the mixing of said solid and liquid components and the application of the setting mass are carried out under vacuum.

* * * * *

UNITED STATES PATENT AND TRADEMARK OFFICE
CERTIFICATE OF CORRECTION

PATENT NO. : 6,075,067
DATED : June 13, 2000
INVENTOR(S) : Lars Ake Alvar Lidgren It is certified that error appears in the above-indentified patent and that said Letters Patent is hereby corrected as shown below:

Column 6, line 31, change "12" to "1"

Signed and Sealed this

Twenty-second Day of May, 2001

Attest:

NICHOLAS P. GODICI

*Attesting Officer*     *Acting Director of the United States Patent and Trademark Office*